(12) United States Patent
Han et al.

(10) Patent No.: US 8,911,954 B2
(45) Date of Patent: Dec. 16, 2014

(54) POLYPEPTIDE LINKER AND METHOD OF ANALYZING TARGET MATERIAL USING THE SAME

(71) Applicant: Samsung Electronics Co., Ltd., Suwon-si (KR)

(72) Inventors: Kyung-yeon Han, Seoul (KR); Yeon-jeong Kim, Yongin-si (KR); Jae-il Lee, Yongin-si (KR); Jeong-gun Lee, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/768,988

(22) Filed: Feb. 15, 2013

(65) Prior Publication Data

US 2014/0065645 A1  Mar. 6, 2014

(30) Foreign Application Priority Data

Aug. 29, 2012 (KR) .................. 10-2012-0095001

(51) Int. Cl.
  *G01N 33/53* (2006.01)
  *C07K 16/46* (2006.01)
  *C07K 16/30* (2006.01)

(52) U.S. Cl.
  CPC ............... *C07K 16/46* (2013.01); *C07K 16/30* (2013.01)
  USPC .......................................... 435/7.1; 435/7.2

(58) Field of Classification Search
  None
  See application file for complete search history.

(56) References Cited

U.S. PATENT DOCUMENTS

| 5,981,200 | A | * | 11/1999 | Tsien et al. ............... 435/7.4 |
| 2005/0191644 | A1 | * | 9/2005 | Shimamoto et al. ........... 435/6 |
| 2005/0255042 | A1 | | 11/2005 | Lam et al. |
| 2009/0041791 | A1 | | 2/2009 | Feng |
| 2009/0220529 | A1 | | 9/2009 | Trouet et al. |
| 2010/0215670 | A1 | | 8/2010 | Cizeau et al. |
| 2010/0317580 | A1 | | 12/2010 | Guenther et al. |
| 2011/0293513 | A1 | | 12/2011 | Govindan et al. |
| 2012/0082617 | A1 | | 4/2012 | Govindan et al. |
| 2013/0202596 | A1 | * | 8/2013 | Salas et al. ............... 424/134.1 |

OTHER PUBLICATIONS

Catanzariti et al. (Protein Science 2004 vol. 13, p. 1331-1339).*
Al-Hajj et al., "Therapeutic implications of cancer stem cells," *Current Opinion in Genetics & Development*, 14: 43-47 (2004).
Ignatiadis et al., "HER2-positive circulating tumor cells in breast cancer," *PLoS ONE*, 6(1):e15624 pp. 1-6 (2011).
Kasimir-Bauer et al., "Expression of stem cell and epithelial-mesenchymal transition markers in primary breast cancer patients with circulating tumor cells," *Breast Cancer Research*, 14(1):R15 pp. 1-9 (2012).
Kim et al., "Highly sensitive proximity mediated immunoassay reveals HER2 status conversion in the circulating tumor cells of metastatic breast cancer patients," *Proteome Science*, 9(1):75 pp. 1-15 (2011).
O'Flaherty et al., "Circulating tumour cells, their role in metastasis and their clinical utility in lung cancer," *Lung Cancer*, 76: 19-25 (2012).

* cited by examiner

*Primary Examiner* — Jacob Cheu
(74) *Attorney, Agent, or Firm* — Leydig, Voit & Mayer, Ltd.

(57) ABSTRACT

A polypeptide linker comprising an antibody-binding region and an enzyme cleavage region, and related compositions, kits, and methods of using same.

15 Claims, 3 Drawing Sheets

(a) Fc-binding - TEV cleavage - Ub mutant - His-tag
    region      region (b)
```
1 atgagaggatcggaaccaatccatcgtagtacgcttacggcactc
    M  R  G  S  E  P  I  H  R  S  T  L  T  A  L  46
  ctagaaaacctgtattttcagggatctggtagtagcggcatgcag
    L  E  N  L  Y  F  Q  G  S  G  S  S  G  M  Q  91
  attttcgtgagaaccctacggggaggaccatcaccctcgaagtt
    I  F  V  R  T  L  T  G  R  T  I  T  L  E  V  136
  gaaccctcggatacgatagaaaatgtaagggccagaatccaggat
    E  P  S  D  T  I  E  N  V  R  A  R  I  Q  D  181
  agggaaggaatacctcctgatcagcagagactgatctttgctggc
    R  E  G  I  P  P  D  Q  Q  R  L  I  F  A  G  226
  aggcagctggaagatggacgtactttgtctgactacaatattcaa
    R  Q  L  E  D  G  R  T  L  S  D  Y  N  I  Q  271
  agggagtctactcttcatcttgtgttgagacttcgtggtgctgga
    R  E  S  T  L  H  L  V  L  R  L  R  G  A  G  316
  ggtcatcaccatcaccatcacggaggttgctaa 348
    G  H  H  H  H  H  H  G  G  C  *
```

POLYPEPTIDE LINKER AND METHOD OF ANALYZING TARGET MATERIAL USING THE SAME

CROSS-REFERENCE TO RELATED APPLICATIONS

This application claims the benefit of Korean Patent Application No. 10-2012-0095001, filed on Aug. 29, 2012, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,683 Byte ASCII (Text) file named "711803_ST25," created on Feb. 5, 2013.

BACKGROUND

1. Field

The present disclosure relates to polypeptide linkers, compositions or kits including the polypeptide linkers, and methods of analyzing a target material using the polypeptide linkers.

2. Description of the Related Art

Cancer metastasis is a process whereby malignant cells from a primary cancer region are transferred to tissues at a distance via blood. Circulating tumor cells (CTCs), which are rare tumor cells that are present in blood vessels and circulate the body, are known to be involved in cancer metastasis with respect to the primary cancer. Even in the case of patients with advanced metastasis, the amount of CTCs in the blood is very small and, thus, it is difficult to separate the CTCs efficiently.

In order to detect and separate cancer cells in a patient's body, cancer cell separation has been studied based on affinity or size of the cells. However, separation by affinity chromatography is so complicated that cancer cells may be lost or have an early detection limit. Also, CTC separation by size filtration may not isolate small cancer cells. In addition, cancer diagnosis does not only simply involve separation and cytometry of cancer cells, but also involves expansion of applications to provide clinically meaningful data for cell analysis, medical research, pharmaceutical research, and disease diagnosis by efficiently separating tumor cells in a biological sample. Based on analysis of proteins or genes of cancer cells, data for diagnosis and prescription is necessary for the purpose of treatment of cancer as well as pretreatment for detection and measurement.

However, an immunofluorescence-based protein assay, wherein proteins of cancer cells are separated by a polymer or a magnetic bead, causes fluorescent signal distortion due to the presence of the bead, so a bead removal step is necessary for reliable analysis. In order to separate the bead from the cancer cells, a method to remove either a binding of an antigen and antibody, or a linker therebetween, may be applied. A physical method, wherein changes in the pH of the solution containing cancer cells cause a decrease in the affinity of antibodies, may damage the cancer cells, and a chemical method performed by a compound is also unsuitable for the diagnosis using molecular analysis.

Therefore, there is still a demand for a method that may be performed without affecting the CTCs to analyze the CTC-surface proteins and intracellular genes.

SUMMARY

Provided are polypeptide linkers comprising, consisting essentially of, or consisting of an antibody-binding region and an enzyme cleavage region, as well as compositions and kits comprising same.

Also provided is a method of analyzing a target material in a sample using a polypeptide linker containing an antibody-binding region and an enzyme cleavage region. The inventive method comprises incubating the sample with the polypeptide linker described above, an antibody that binds to the target material, and a microparticle to form a complex; isolating the complex; (d) incubating the complex and an enzyme that recognizes the enzyme cleavage region to cut the polypeptide linker at the enzyme cleavage region, which results in separation of the microparticle from the complex, and (e) removing the microparticle.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the invention.

A polypeptide linker comprising, consisting essentially of, or consisting of an antibody-binding region and an enzyme cleavage region is provided herein.

The antibody-binding region may be a binding region of an Fc region (fragment crystallizable) of an antibody. The binding region of an Fc region may be described as an Fc-binding region or an Fc-binding peptide. An Fc region of an antibody is a terminal region of the antibody interacting with a cell surface receptor known as an Fc receptor, and with some proteins of the complement system. The Fc region refers to protein fragments derived from the second (CH2) and the third (CH3) constant domain in a heavy chain. In one embodiment, the binding region of an Fc region of the antibody is a fragment of the Fc receptor. In another embodiment, the binding region of an Fc region of the antibody is a polypeptide linker comprising the amino acid sequence of SEQ ID NO: 1.

The enzyme cleavage region may be a region to be cut by a protease, in other words, a polypeptide comprising a protease recognition sequence or "site" that is cleavable by a protease when present. The term "protease" is used interchangeably with the term "peptidase" or the term "proteinase". Protease is an enzyme that is used to cut peptide bonds between the amino acids. For example, protease may be serine protease, threonine protease, cysteine protease, aspartate protease, metalloprotease, glutamic acid protease, or a combination thereof. Alternatively, protease may be tobacco etch virus (TEV) protease, trypsin, chymotrypsin, elastase, pepsin, enteropeptidase, or a combination thereof. The protease recognition sites for each of these proteases is known in the art. The enzyme cleavage region may vary depending on enzymes, or may be known to those of ordinary skill in the art. For example, the enzyme cleavage region may be a polypeptide comprising the amino acid sequence of SEQ ID NO: 2.

The polypeptide linker including an antibody-binding region and an enzyme cleavage region may be arranged in order of the antibody-binding region and the enzyme cleavage region from the N-terminal. Alternatively, the polypeptide linker may be arranged in order of the enzyme cleavage region and the antibody-binding region from the N-terminal.

The polypeptide linker may further include one or more (e.g., 1, 2, 3, 4, or more) spacer polypeptides positioned between the antibody-binding region and the enzyme cleavage region and/or at the end of the enzyme cleavage region opposite the antibody binding region. Each spacer polypeptide may be a polypeptide consisting of 1 to 100, 1 to 80, 1 to 60, 1 to 40, 1 to 21, or 1 to 10 amino acids. Any spacer polypeptide can be used in the invention. In one embodiment, the spacer polypeptide includes one or more glycine residues. For example, the spacer polypeptide may be a polypeptide comprising or consisting of the amino acid sequence of GS or GSSG (SEQ ID NO: 3).

The polypeptide linker may further include an ubiquitin. For example, ubiquitin may be positioned between the antibody-binding region and the enzyme cleavage region. When a spacer polypeptide is positioned between the antibody binding region and the enzyme cleavage region, the ubiquitin may be positioned between the antibody binding region and the spacer, or between the spacer and the enzyme cleavage region. Alternatively, or in addition, ubiquitin may be positioned at the end of the enzyme cleavage region opposite the antibody-binding region, optionally spaced apart from the enzyme cleavage region by a spacer peptide. Although not wishing to be bound by any particular theory, the ubiquitin may improve the cleavage efficiency of the polypeptide linker by increasing accessibility of the enzymes. The ubiquitin, for example, may be a polypeptide comprising or consisting of the amino acid sequence of SEQ ID NO: 6.

Also provided is a composition useful for analyzing a target material in a sample, wherein the composition comprises, consists essentially of, or consists of a polypeptide linker comprising, consisting essentially of, or consisting of an antibody-binding region and an enzyme cleavage region and a solid support. The composition is, optionally, in a dry form (e.g., a solid, such as a powder or granular solid) or in a liquid composition comprising a suitable carrier.

The sample may be a biological sample, such as a body fluid or tissue sample including, but not limited to, a blood, a marrow fluid, lymph, saliva, a lachrymal fluid, urine, a mucous membrane fluid, an amniotic fluid, or a combination thereof. The biological sample, for example, may be a cell, a cell culture, or a combination thereof.

The target material may be a target cell or material contained in or on the cell. For example, the target material may be cell surface proteins of the target cell, intracellular proteins, intracellular nucleic acids, or a combination thereof. The target cell may be a tumor cell. The tumor cell, for example, may be a primary cancer cell, a circulating tumor cell (CTC), a metastatic cancer cell, or a combination thereof.

The invention also provides a kit for analyzing a target material in a sample comprising, consisting essentially of, or consisting of a polypeptide linker comprising, consisting essentially of, or consisting of an antibody-binding region and an enzyme cleavage region, and a solid support, an enzyme that cleaves the enzyme cleavage region, or both. The polypeptide linker and enzyme may, optionally, be provided in a dry form (e.g., a powder or granular solid) separately or together, or in individual compositions with a suitable carrier.

A method for analysis of a target material contained in a sample also is provided, wherein the method comprises, consists essentially of, or consists of incubating a sample comprising a target material with an antibody that binds to the target material, the polypeptide linker described herein, and a microparticle to form a complex; isolating the complex from the sample; and incubating the complex and an enzyme that recognizes the enzyme cleavage region so as to cut the polypeptide linker at the enzyme cleavage region, which results in separation of the microparticle from the complex. Once the microparticle is separated and, optionally, removed from the composition comprising the target material, the remaining portion of the complex is ready for analysis.

The antibody may be an intact antibody, a partial antibody, a fragment of the antibody, or a combination thereof.

The intact antibody may be a polyclonal or monoclonal antibody. According to a method known to those of ordinary skill in the art, the polyclonal antibody may be prepared by injecting biomarker protein, which is an antigen, or a fragment thereof into an external host. The external host may be a mammal such as a mouse, a rat, a sheep, or a rabbit. When injecting the antigen via intramuscular, intraperitoneal, or subcutaneous injection, an adjuvant may be generally injected together to improve antigenecity. Then, the blood is regularly taken from the external host to collect serum that shows improved titer and specificity to an antigen, and to separate and purify antibodies therein. The monoclonal antibody may be prepared by using a technique to produce immortalized cell lines by fusion, which is known to those of ordinary skill in the art. A brief description of a method of preparing a monoclonal antibody is as follows. An appropriate amount (approximately 10 μg) of the protein is used to immunize Balb/C mice after protein purification, or a synthesized polypeptide fragment of the protein is bound to bovine serum albumin and used to immunize the mice. Then, antibody-producing lymphocytes separated from the mice are fused with myeloma of human or mice to produce immortalized hybridoma. By using an ELISA method, the hybridoma cells that produce desired monoclonal antibodies are selectively proliferated to separate and purify the monoclonal antibodies only from the culture.

A part or a fragment of antibodies, as a fragment of the intact structure of immunoglobulin, refers to a part of a polypeptide including an antigen-binding region such as scFv, (scFv)2, Fab, Fab', F(ab')2, or a combination thereof. Fab has one antigen-binding region with a structure having variable domains from one light chain and one heavy chain, and a constant domain from one light chain and the first constant domain (CH1) of one heavy chain. Fab' with a hinge region that includes at least one cysteine residue at the C-terminal of the CH1 domains from the heavy chains is different from Fab. F(ab')2 antibody is formed by a disulfide bond with cysteine residues of the hinge region in Fab'. Fv is a minimum fragment of an antibody with variable domains from one heavy chain and one light chain, and a recombinant method to produce an Fv fragment is widely known to those of ordinary skill in the art. A two-chain Fv has a variable domain from one heavy chain and a variable domain from one light chain by a noncovalent bond, and a single-chain Fv has a variable domain from one heavy chain and a variable domain from one light chain by a covalent bond through a peptide linker, or the variable domains are directly linked at the C-terminal to have a dimer structure like the two-chain Fv. The antigen-binding fragment may be obtained by using proteolytic enzymes (e.g., a intact antibody is restricted by papain to obtain Fab, and is restricted by pepsin to obtain F(ab')2 fragment) or may be recombinantly produced.

The antibody may include a label that generates a detectable signal. The label, for example, may be a chemical (e.g., biotin), an enzyme (e.g., alkaline phosphatase, β-galactosidase, horseradish peroxidase and cytochrome P450), a radioactive material (e.g., C14, I125, P32 and S35), a fluorescent material (e.g., fluorescein), an illuminescent material, a chemiluminescent material, a fluorescence resonance energy transfer (FRET) material, or a combination thereof.

Incubation of the sample with the antibody that is capable of binding to the target material, the polypeptide linker including an antibody-binding region and an enzyme cleavage region, and the microparticle to form the complex may be conducted in vitro for any suitable period of time and under any suitable conditions, so long as the complex is formed. For example, the incubation may be performed at room temperature.

The microparticle may be a polymer particle or a magnetic particle. For example, the microparticle may be a hydrocarbon polymer (e.g., polystyrene and polypropylene), glass, metal, or gel may be used. The microparticle may be linear, spherical, or polygonal. The linear microparticle may be a bead.

The method may include the isolation of the complex from other components of the biological sample. Any suitable means of isolating the complex can be employed. For example, when the microparticle is a bead (e.g., magnetic bead), the complex can be isolated (separated from some or all other components of the sample) on the basis of physical or chemical properties of the bead (e.g., separation based on size, weight, affinity, magnetic properties, etc.). As used herein, "isolated" does not imply complete or total isolation or purification, and encompasses isolation or purification to any degree, including partial or "crude" isolation or purification as well as complete or nearly complete purification or isolation.

The method may include the incubation of the complex with an enzyme that recognizes an enzyme cleavage region to cut the linker polypeptide, which results in separation of the microparticle from the remaining portion of the complex.

Incubation of the complex and the enzyme may be conducted in vitro for any suitable period of time and under any suitable conditions, such that the linker polypeptide is cut and the microparticle is separated from the remaining portion of the complex.

The method may include the removal of the microparticle from a composition comprising the remaining portion of the complex after cleavage with the enzyme. The microparticle can be removed by any suitable means. For example, when the microparticle is a bead (e.g., magnetic bead), the complex can be isolated (separated from other components) on the basis of physical or chemical properties of the bead (e.g., separation based on size, weight, affinity, magnetic properties, etc.).

The method may further include a washing step. For example, the method may further include a washing step after the formation of the complex, the incubation of the complex and the enzyme, or a combination thereof.

By preventing signal distortion that may be caused by the microparticle when analyzing the target material, the inventive method is believed to be useful in improving the reliability and the accuracy of the subsequent analysis of proteins (e.g., CTC-surface proteins) and intracellular genes in the target material in the sample, thereby leading to a more accurate and reliable diagnosis.

One or more embodiments of the invention will now be described in detail with reference to the following examples. However, these examples are not intended to limit the scope of the one or more embodiments of the invention.

EXAMPLE 1

Preparation of a Polypeptide Linker

Figure 1A:
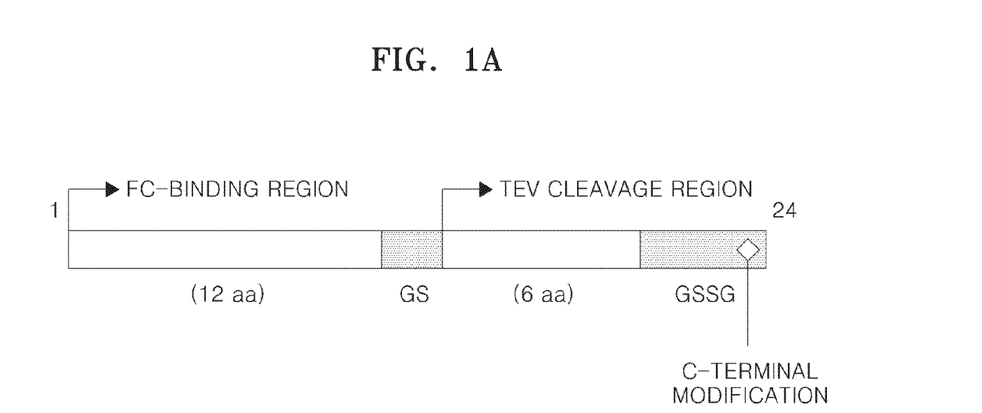
FIG. 1A is a schematic diagram illustrating a polypeptide linker including an Fc-binding region, a cleavage region by TEV protease, and spacer polypeptides (GS and GSSG (SEQ ID NO: 3)).
Figure 1B:
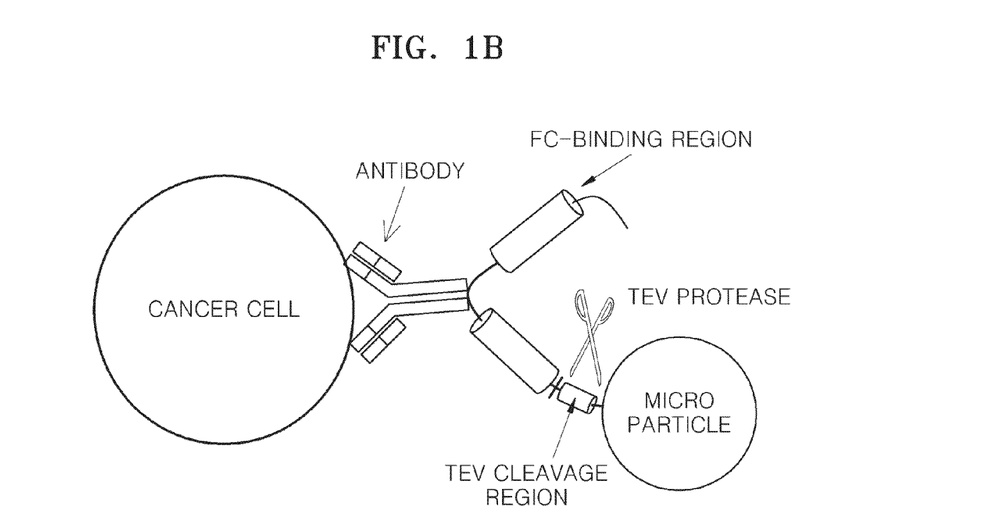
FIG. 1B is a schematic diagram illustrating a complex of a cancer cell, an antibody, the polypeptide linker comprised of an Fc-binding region and a cleavage region by TEV protease, and a bead (microparticle).

A polypeptide linker including an Fc-binding region, a TEV protease cleavage region, and a spacer polypeptide were prepared (PEPTRON, Inc., Korea) (see FIG. 1A), wherein the Fc-binding region, TEV protease cleavage region, spacer polypeptide, and polypeptide linker sequences are as follows:

Fc-binding region: N-terminal-EPIHRSTLTALL-C-terminal (SEQ ID NO: 1).

TEV protease cleavage region: N-terminal-ENLYFQ-C-terminal (SEQ ID NO: 2).

Spacer polypeptides: N-terminal-GS-C-terminal or N-terminal-GSSG-C-terminal (SEQ ID NO: 3).

Polypeptide linker: N-terminal-EPIHRSTLTALLGSSGENLYFQGSSGK-C terminal (SEQ ID NO: 4).

A Lysine (K) residue was added to the C-terminus of the polypeptide linker for chemical linkage (1-ethyl-3-[3-dimethylaminopropyl]carbodiimide hydrochloride (EDC) coupling) to a bead.

Figure 2:
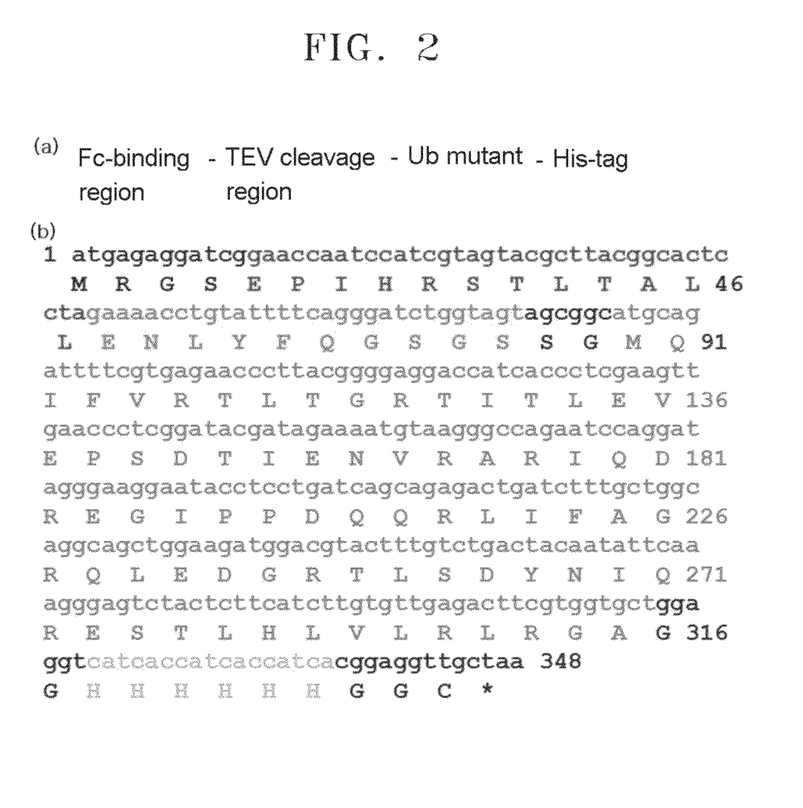
FIG. 2A is a schematic diagram illustrating a linker to which a ubiquitin mutant and His-tag are bound.
FIG. 2B is the nucleic acid encoding the polypeptide linker with ubiquitin mutant and His-tag (SEQ ID NO: 5).

Additionally, a nucleotide sequence (SEQ ID NO: 5) that encodes a polypeptide linker comprising an Fc-binding region, a TEV cleavage region, spacer polypeptides, a ubiquitin, and a histidine tag was prepared. The polypeptide linker (recombinant protein) including ubiquitin was prepared (Genotech Corp.) (FIG. 2).

The amino acid sequences of the Fc-binding region, the TEV cleavage region, and the spacer polypeptide are described above. The amino acid sequence of ubiquitin and the polypeptide linker comprising the ubiquitin are as follows:

Ubiquitin: N-terminal-MQIFVRTLTGRTITLEVEPSDTIENVRARIQDREGIPPDQQRLIFAGRQLEDRTLSDYNIQRESTLHLVLRLRGA-C-terminal (SEQ ID NO: 6).

Polypeptide linker comprising ubiquitin: N-terminal-MRGSEPIHRSTLTALLENLYFQGSGSSGMQIFVRTLTGRTITLEVEPSDTIENVRARIQDREGIPPDQQRLIFAGRQLEGRTLSDYNIQRESTLHLVLRLRGAGGHHHHHHGGC-C-terminal (SEQ ID NO: 7).

EXAMPLE 2

Cleavage of a Polypeptide Linker by a TEV Protease

A polypeptide linker was labeled with N-terminal fluorescein iso-thio-cyanate (FITC) (PEPTRON, Inc., Korea).

A complex of a FITC-labeled polypeptide linker and a bead was prepared by a coupling method with 1-ethyl-3(3-dimethylamiopropyl)carbodiimide (EDC)/N-terminal-hydroxy succinimide (NHS). In particular, a polypeptide linker labeled with a bead, 375 µg/mL EDC, 575 µg/mL N-terminal-hydroxy succinimide (NHS) and 1 mg/mL FITC-labeled polypeptide linker was incubating with rotation for more than 3 hours at room temperature. Then, the linker was washed 3 times with 2% (w/v) PBS, suspended in a BSA solution, and kept refrigerated.

An initial fluorescence signal of the complex of the FITC-labeled polypeptide linker and the bead was measured by fluorescence microscopy. TEV protease was added to the complex of the polypeptide linker and the bead at a ratio of 1:1 or 1:2 compared to the mass of the polypeptide linker. The fluorescence signal was measured after 1 hour incubation at room temperature. A large fluorescence indicates that a signal was amplified or distorted by a condensed bead.

Cleavage efficiency of the polypeptide linker depending on the concentration of the TEV protease is shown in Table 1.

TABLE 1

|  | Intensity of Background Signal | Intensity of Signal | Ratio of Signal/Background Signal |
| --- | --- | --- | --- |
| Initial Fluorescence Signal | 4.14 | 7.33 | 1.77 |
| 1:1 TEV Protease | 8.35 | 10.33 | 1.24 |
| 1:2 TEV Protease | 8.31 | 9 | 1.08 |

Most polypeptide linkers were cleaved when the mass of the added enzyme was twice the mass of the polypeptide linker.

EXAMPLE 3

Binding of a Bead and an Antibody using a Polypeptide Linker

A mouse-derived antibody that recognizes EpCAM protein, wherein the protein is excessively expressed in the breast cancer cell line (MCF7), was bound to the polypeptide linker prepared as described in Example 1.

In particular, a bead, 375 µg/mL EDC, 575 µg/mL N-terminal-hydroxy succinimide (NHS) and 1 mg/mL linker polypeptide incubated with rotation for more than 2 hours at room temperature. Then, the reactant was washed 3 times with PBS. After adding anti-EpCAM antibody in 200 µg/500 ul PBS (R&D systems) and 1 hour incubation at room temperature, the reactant was incubated overnight in a refrigerated condition. Then, the reactant was washed again 3 times with PBS. After blocking with 5% (w/v) BSA, the linker was suspended in a 2% (w/v) BSA solution and kept refrigerated.

EXAMPLE 4

Bead Removal from Cancer Cells by using TEV Protease

Figure 3:
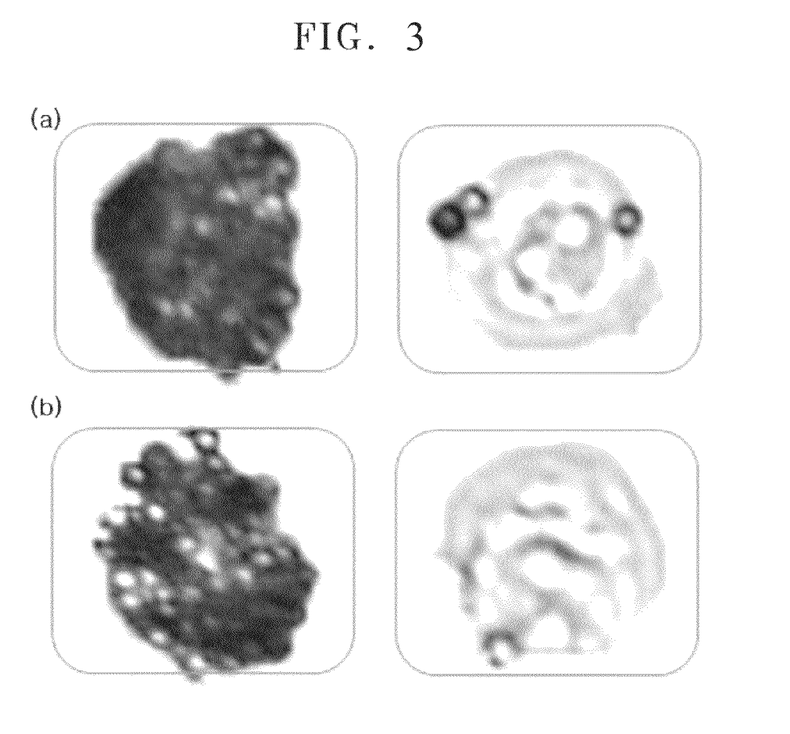
FIG. 3A illustrates cancer cells before/after removing the bound beads.
FIG. 3B illustrates cancer cells after removing the bound beads.

The complex comprising the polypeptide linker, bead, and antibody prepared as described in Example 3, as well as $5 \times 10^5$ cells/mL of MCF7 cancer cells, were incubated for 10 minutes at room temperature. TEV protease was added, and the resultant mixture was incubated for 30 min at room temperature. The remaining beads on the surface of the cancer cell was confirmed by microscopy (FIGS. 3A and 3B).

As a result, the beads were confirmed to be removed from the surface of the cancer cell.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting a target material in a sample, the method comprising:
   (a) incubating a sample with
      (i) an antibody that binds to a target material in the sample, wherein the antibody comprises an Fc region, and
      (ii) a polypeptide linker comprising an Fc-binding region and an enzyme cleavage region, wherein a microparticle is coupled to the polypeptide linker, to form a complex;
   (b) isolating the complex based on the physical or chemical properties of the microparticle;
   (c) incubating the complex with an enzyme that recognizes the enzyme cleavage region to cut the polypeptide linker at the enzyme cleavage region, which results in separation of the microparticle from the complex; and
   (d) detecting the complex without the microparticle, thereby detecting the target material in the sample.

2. The method of claim 1, wherein the sample is a biological sample.

3. The method of claim 1, wherein the sample is blood, bone marrow, lymph, saliva, lachrymal fluid, urine, mucous, amniotic fluid, or a combination thereof.

4. The method of claim 1, wherein the antibody is an antibody fragment.

5. The method of claim 1, wherein the target material is a cell.

6. The method of claim 5, wherein the target material is a tumor cell.

7. The method of claim 5, wherein the target material is a circulating tumor cell.

8. The method of claim 1, wherein the microparticle is a polymer bead or a magnetic bead.

9. The method of claim 1, further comprising
   (a1) washing after the formation of the complex,
   (a2) washing after incubating the complex and the enzyme, or
   (a3) a combination of (a1) and (a2).

10. The method of claim 1, wherein the enzyme cleavage region comprises a protease recognition sequence.

11. The method of claim 10, wherein the protease recognition sequence is a sequence recognized by tobacco etch virus (TEV) protease, trypsin, chymotrypsin, elastase, pepsin, enteropeptidase, or a combination thereof.

12. The method of claim 1, wherein the polypeptide linker further comprises at least one spacer polypeptide positioned between the Fc-binding region and the enzyme cleavage region, at the end of the enzyme cleavage region opposite the Fc-binding region, or both.

13. The method of claim 1, wherein the polypeptide linker further comprises an ubiquitin.

14. The method of claim 1, wherein the polypeptide linker further comprises a fluorescent label.

15. The method of claim 14, wherein the fluorescent label is fluorescein iso-thio-cyanate (FITC).

* * * * *

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Synthetic (Fc binding region)

<400> SEQUENCE: 1

Glu Pro Ile His Arg Ser Thr Leu Thr Ala Leu Leu
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic (TEV protease cleavage region)

<400> SEQUENCE: 2

Glu Asn Leu Tyr Phe Gln
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic (Spacer)

<400> SEQUENCE: 3

Gly Ser Ser Gly
1

<210> SEQ ID NO 4
<211> LENGTH: 27
<212> TYPE: PRT
<213> ORGANISM: Artificial Sequence
<220> FEATURE:
<223> OTHER INFORMATION: Synthetic (Linker polypeptide)

<400> SEQUENCE: 4

Glu Pro Ile His Arg Ser Thr Leu Thr Ala Leu Leu Gly Ser Ser Gly
1               5                   10                  15

Glu Asn Leu Tyr Phe Gln Gly Ser Ser Gly Lys
            20                  25

<210> SEQ ID NO 5
<211> LENGTH: 348
<212> TYPE: DNA
<213> ORGANISM: Artificial Sequence
<220> FEATURE:
<223> OTHER INFORMATION: Synthetic (DNA encoding Linker polypeptide)

<400> SEQUENCE: 5
atgagaggat cggaaccaat ccatcgtagt acgcttacgg cactcctaga aaacctgtat      60
tttcagggat ctggtagtag cggcatgcag attttcgtga aacccttac ggggaggacc     120 atcaccctcg aagttgaacc ctcggatacg atagaaaatg taagggccag aatccaggat     180
gaaccctcgg atacgataga aaatgtaagg gccagaatcc aggataggca gctggaagat     240
ggacgtactt tgtctgacta caatattcaa agggagtcta ctcttcatct tgtgttgaga     300
cttcgtggtg ctggaggtca tcaccatcac catcacggag gttgctaa                  348

<210> SEQ ID NO 6
<211> LENGTH: 76
<212> TYPE: PRT
<213> ORGANISM: Artificial Sequence
<220> FEATURE:
<223> OTHER INFORMATION: Synthetic (Ubiquitin)

```
<400> SEQUENCE: 6

Met Gln Ile Phe Val Arg Thr Leu Thr Gly Arg Thr Ile Thr Leu Glu
1               5                   10                  15

Val Glu Pro Ser Asp Thr Ile Glu Asn Val Arg Ala Arg Ile Gln Asp
                20                  25                  30

Arg Glu Gly Ile Pro Pro Asp Gln Gln Arg Leu Ile Phe Ala Gly Arg
            35                  40                  45

Gln Leu Glu Asp Gly Arg Thr Leu Ser Asp Tyr Asn Ile Gln Arg Glu
    50                  55                  60

Ser Thr Leu His Leu Val Leu Arg Leu Arg Gly Ala
65                  70                  75

<210> SEQ ID NO 7
<211> LENGTH: 115
<212> TYPE: PRT
<213> ORGANISM: Artificial Sequence
<220> FEATURE:
<223> OTHER INFORMATION: Synthetic (Linker polypeptide)

<400> SEQUENCE: 7

Met Arg Gly Ser Glu Pro Ile His Arg Ser Thr Leu Thr Ala Leu Leu
1               5                   10                  15

Glu Asn Leu Tyr Phe Gln Gly Ser Gly Ser Ser Gly Met Gln Ile Phe
                20                  25                  30

Val Arg Thr Leu Thr Gly Arg Thr Ile Thr Leu Glu Val Glu Pro Ser
            35                  40                  45

Asp Thr Ile Glu Asn Val Arg Ala Arg Ile Gln Asp Arg Glu Gly Ile
    50                  55                  60

Pro Pro Asp Gln Gln Arg Leu Ile Phe Ala Gly Arg Gln Leu Glu Asp
65                  70                  75                  80

Gly Arg Thr Leu Ser Asp Tyr Asn Ile Gln Arg Glu Ser Thr Leu His
                85                  90                  95

Leu Val Leu Arg Leu Arg Gly Ala Gly Gly His His His His His His
                100                 105                 110

Gly Gly Cys
        115
```